(12) United States Patent
Montclare et al.

(10) Patent No.: US 9,370,491 B2
(45) Date of Patent: Jun. 21, 2016

(54) POLYMER CARRIER

(75) Inventors: Jin Kim Montclare, New York, NY (US); Man Xia Lee, Brooklyn, NY (US); Jennifer Haghpanah, Newton, CT (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/450,790

(22) Filed: Apr. 19, 2012

(65) Prior Publication Data

US 2012/0251591 A1    Oct. 4, 2012

Related U.S. Application Data

(60) Division of application No. 13/163,299, filed on Jun. 17, 2011, now Pat. No. 8,790,709, which is a continuation of application No. 12/141,192, filed on Jun. 18, 2008.

(60) Provisional application No. 60/944,545, filed on Jun. 18, 2007.

(51) Int. Cl.
    *C07K 1/113*    (2006.01)
    *A61K 9/00*     (2006.01)
    *A61K 9/16*     (2006.01)

(52) U.S. Cl.
    CPC .................................. *A61K 9/1658* (2013.01)

(58) Field of Classification Search
    None
    See application file for complete search history.

(56) References Cited

U.S. PATENT DOCUMENTS

| | | | |
|---|---|---|---|
| 7,030,208 | B2 | 4/2006 | Yalpani |
| 2002/0164810 | A1 | 11/2002 | Dukor et al. |
| 2003/0003135 | A1 | 1/2003 | Leung et al. |
| 2004/0115180 | A1* | 6/2004 | Abdelouahed ............... 424/94.1 |

OTHER PUBLICATIONS

"Engineered Protein Polymers," Cho, H., et al., Polymer Preprints (American Chemical Society, Division of Polymer Chemistry) 47(2): 227-228 (Sep. 2006).*

"All-trans retinol, vitamin D and other hydrophobic compounds bind in the axial pore of the five-stranded coiled-coil domain of cartilage oligomeric matrix protein," Guo, Y., et al., EMBO Journal 17(18): 5265-5272 (1998).*

Megeed, Z., et al., "Genetically Engineered silk-elastinlike protein polymers for controlled drug delivery," Advanced Drug Delivery Reviews 54: 1075-1091 (2002).*

Nuhn, H. and Klok, Harm-Anton, Secondary Structure Formation and LCST Behavior of Short Elastin-Like Peptides, Biomacromolecules 2008, pp. 2755-2763, vol. 9, No. 10, American Chemical Society.

Trabbic-Carlson, K. et al., Effect of protein fusion on the transition temperature of an environmentally responsive elastin-like polypeptide: a role for surface hydrophobicity, Protein Engineering, Design & Selection 2004, pp. 57-66, vol. 17, No. 1, Oxford University Press.

Haghpanah et al., Artificial Protein Block Copolymers Blocks Comprising Two Distinct Self-Assembling Domains, ChemBioChem, 10: 2733-35. Jan. 1, 2009.

Kotze et al., Chitosans for enhanced delivery of therapeutic peptides across intestinal epithelia: in vitro evaluation in Caco-2 cell monolayers, International Journal of Pharmaceutics, 159: 243-53. Jan. 1, 1997.

Shih et al., The production of poly(y-glutamic acid) from microorganisms and its various applications, Bioresource Technoogy, 79(3): 207-25. Jan. 1, 2001.

\* cited by examiner

*Primary Examiner* — David J Blanchard
*Assistant Examiner* — Daniel F Coughlin
(74) *Attorney, Agent, or Firm* — Hodgson Russ LLP

(57) ABSTRACT

Compositions and methods for delivering bioactive agents, such as vitamins, hormones, nutrients and drugs, by stabilizing and or solubilizing these agents in a polymer matrix. The carrier polymers can be used in drug delivery and are useful for delivery of small molecules. The carrier polymers also can be used in scaffolds for regenerative medicine.

13 Claims, 7 Drawing Sheets

SEQUENCE LISTING

```
<160> NUMBER OF SEQ ID NOS: 17

<210> SEQ ID NO 1
<211> LENGTH: 61
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Arg Gly Ser His His His His His His Gly Ser Gly Asp Leu Ala
1               5                   10                  15

Pro Gln Met Leu Arg Glu Leu Gln Glu Thr Asn Ala Ala Leu Gln Asp
            20                  25                  30

Val Arg Glu Leu Leu Arg Gln Gln Val Lys Glu Ile Thr Phe Leu Lys
        35                  40                  45

Asn Thr Val Met Glu Cys Asp Ala Cys Gly Lys Leu Asn
    50                  55                  60

<210> SEQ ID NO 2
<211> LENGTH: 49
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Cys Asp Ala Cys Gly Lys Leu
        35                  40                  45

Asn

<210> SEQ ID NO 3
<211> LENGTH: 59
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Met Arg Gly Ser His His His His His His Gly Asp Leu Ala Pro Gln
1               5                   10                  15

Met Leu Arg Glu Leu Gln Glu Thr Asn Ala Ala Leu Gln Asp Val Arg
            20                  25                  30

Glu Leu Leu Arg Gln Gln Val Lys Glu Ile Thr Phe Leu Lys Asn Thr
        35                  40                  45

Val Met Glu Cys Asp Ala Cys Gly Lys Leu Asn
    50                  55

<210> SEQ ID NO 4
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Arg Gly Ser His His His His His His Gly Asp Leu Ala Pro Gln
1               5                   10                  15

Met Leu Arg Glu Leu Gln Glu Thr Asn Ala Ala Leu Gln Asp Val Arg
            20                  25                  30

Glu Leu Leu Arg Gln Gln Val Lys Glu Ile Thr Phe Leu Lys Asn Thr
        35                  40                  45

Val Met Glu Ser Asp Ala Ser Gly Lys Leu Asn
    50                  55

<210> SEQ ID NO 5
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Arg Gly Ser His His His His His His Gly Asp Leu Ala Pro Gln
1               5                   10                  15

Met Leu Arg Glu Ala Gln Glu Thr Asn Ala Ala Leu Gln Asp Val Arg
            20                  25                  30

Glu Leu Leu Arg Gln Gln Val Lys Glu Ile Thr Phe Leu Lys Asn Thr
        35                  40                  45

Val Met Glu Ser Asp Ala Ser Gly Lys Leu Asn
    50                  55

<210> SEQ ID NO 6
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Arg Gly Ser His His His His His His Gly Asp Leu Ala Pro Gln
1               5                   10                  15

Met Leu Arg Glu Leu Gln Glu Ala Asn Ala Ala Leu Gln Asp Val Arg
```

```
                20                  25                  30

Glu Leu Leu Arg Gln Gln Val Lys Glu Ile Thr Phe Leu Lys Asn Thr
            35                  40                  45

Val Met Glu Ser Asp Ala Ser Gly Lys Leu Asn
    50                  55

<210> SEQ ID NO 7
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Arg Gly Ser His His His His His His Gly Asp Leu Ala Pro Gln
1               5                   10                  15

Met Leu Arg Glu Leu Gln Glu Thr Asn Ala Ala Ala Gln Asp Val Arg
            20                  25                  30

Glu Leu Leu Arg Gln Gln Val Lys Glu Ile Thr Phe Leu Lys Asn Thr
            35                  40                  45

Val Met Glu Ser Asp Ala Ser Gly Lys Leu Asn
    50                  55

<210> SEQ ID NO 8
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Arg Gly Ser His His His His His His Gly Asp Leu Ala Pro Gln
1               5                   10                  15

Met Leu Arg Glu Leu Gln Glu Thr Asn Ala Ala Leu Gln Asp Ala Arg
            20                  25                  30

Glu Leu Leu Arg Gln Gln Val Lys Glu Ile Thr Phe Leu Lys Asn Thr
            35                  40                  45

Val Met Glu Ser Asp Ala Ser Gly Lys Leu Asn
    50                  55

<210> SEQ ID NO 9
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Arg Gly Ser His His His His His His Gly Asp Leu Ala Pro Gln
1               5                   10                  15

Met Leu Arg Glu Leu Gln Glu Thr Asn Ala Ala Leu Gln Asp Val Arg
            20                  25                  30

Glu Leu Ala Arg Gln Gln Val Lys Glu Ile Thr Phe Leu Lys Asn Thr
            35                  40                  45

Val Met Glu Ser Asp Ala Ser Gly Lys Leu Asn
    50                  55

<210> SEQ ID NO 10
```

<211> LENGTH: 59
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Met Arg Gly Ser His His His His His His Gly Asp Leu Ala Pro Gln
1               5                   10                  15

Met Leu Arg Glu Leu Gln Glu Thr Asn Ala Ala Leu Gln Asp Val Arg
            20                  25                  30

Glu Leu Leu Arg Gln Ala Val Lys Glu Ile Thr Phe Leu Lys Asn Thr
        35                  40                  45

Val Met Glu Ser Asp Ala Ser Gly Lys Leu Asn
    50                  55

<210> SEQ ID NO 11
<211> LENGTH: 59
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Met Arg Gly Ser His His His His His His Gly Asp Leu Ala Pro Gln
1               5                   10                  15

Met Leu Arg Glu Leu Gln Glu Thr Asn Ala Ala Leu Gln Asp Val Arg
            20                  25                  30

Glu Leu Leu Arg Gln Gln Val Lys Glu Ala Thr Phe Leu Lys Asn Thr
        35                  40                  45

Val Met Glu Ser Asp Ala Ser Gly Lys Leu Asn
    50                  55

<210> SEQ ID NO 12
<211> LENGTH: 59
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Met Arg Gly Ser His His His His His His Gly Asp Leu Ala Pro Gln
1               5                   10                  15

Met Leu Arg Glu Leu Gln Glu Thr Asn Ala Ala Leu Gln Asp Val Arg
            20                  25                  30

Glu Leu Leu Arg Gln Gln Val Lys Glu Ile Thr Phe Ala Lys Asn Thr
        35                  40                  45

Val Met Glu Ser Asp Ala Ser Gly Lys Leu Asn
    50                  55

<210> SEQ ID NO 13
<211> LENGTH: 59
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Met Arg Gly Ser His His His His His His Gly Asp Leu Ala Pro Gln

```
                1               5                   10                  15
Met Leu Arg Glu Leu Gln Glu Thr Asn Ala Ala Leu Gln Asp Val Arg
                20                  25                  30

Glu Leu Leu Arg Gln Gln Val Lys Glu Ile Thr Phe Leu Lys Asn Thr
            35                  40                  45

Ala Met Glu Ser Asp Ala Ser Gly Lys Leu Asn
        50                  55

<210> SEQ ID NO 14
<211> LENGTH: 59
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Arg Gly Ser His His His His His Gly Asp Leu Ala Pro Gln
1               5                   10                  15

Met Leu Arg Glu Leu Gln Glu Thr Asn Ala Ala Leu Gln Asp Val Arg
                20                  25                  30

Glu Leu Leu Arg Gln Gln Val Lys Glu Ile Thr Phe Leu Lys Asn Thr
            35                  40                  45

Val Met Glu Ala Asp Ala Ser Gly Lys Leu Asn
        50                  55

<210> SEQ ID NO 15
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Arg Gly Ser His His His His His His Gly Ser Lys Pro Ile Ala
1               5                   10                  15

Ala Ser Ala Val Pro Gly Val Gly Val Pro Gly Val Gly Val Pro Gly
                20                  25                  30

Phe Gly Val Pro Gly Val Gly Val Pro Gly Val Gly Val Pro Gly Val
            35                  40                  45

Gly Val Pro Gly Val Gly Val Pro Gly Phe Gly Val Pro Gly Val Gly
        50                  55                  60

Val Pro Gly Val Gly Val Pro Gly Val Gly Val Pro Gly Val Gly Val
65                  70                  75                  80

Pro Gly Phe Gly Val Pro Gly Val Gly Val Pro Gly Val Gly Val Pro
                85                  90                  95

Gly Val Gly Val Pro Gly Val Gly Val Pro Gly Phe Gly Val Pro Gly
            100                 105                 110

Val Gly Val Pro Gly Val Gly Val Pro Gly Val Gly Val Pro Gly Val
        115                 120                 125

Gly Val Pro Gly Phe Gly Val Pro Gly Val Gly Val Pro Gly Val Gly
        130                 135                 140

Val Pro Leu Glu Gly Ser Glu Leu Ala Ala Thr Ala Thr Ala Thr Ala
145                 150                 155                 160

Thr Ala Thr Ala Thr Ala Ala Cys Gly Asp Leu Ala Pro Gln Met Leu
                165                 170                 175

Arg Glu Leu Gln Glu Thr Asn Ala Ala Leu Gln Asp Val Arg Glu Leu
```

```
                    180                 185                 190
Leu Arg Gln Gln Val Lys Glu Ile Thr Phe Leu Lys Asn Thr Val Met
            195                 200                 205

Glu Ser Asp Ala Ser Gly Leu Gln Ala Ala Thr Ala Thr Ala Thr Ala
        210                 215                 220

Thr Ala Thr Ala Thr Ala Val Asp Leu Gln Pro Ser
225                 230                 235

<210> SEQ ID NO 16
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Arg Gly Ser His His His His His His Gly Ser Ala Cys Glu Leu
1               5                   10                  15

Ala Ala Thr Ala Thr Ala Thr Ala Thr Ala Thr Ala Thr Ala Ala Cys
            20                  25                  30

Gly Asp Leu Ala Pro Gln Met Leu Arg Glu Leu Gln Glu Thr Asn Ala
        35                  40                  45

Ala Leu Gln Asp Val Arg Glu Leu Leu Arg Gln Gln Val Lys Glu Ile
    50                  55                  60

Thr Phe Leu Lys Asn Thr Val Met Glu Ser Asp Ala Ser Gly Leu Gln
65                  70                  75                  80

Ala Ala Thr Ala Thr Ala Thr Ala Thr Ala Thr Ala Thr Ala Val Asp
                85                  90                  95

Lys Pro Ile Ala Ala Ser Ala Val Pro Gly Val Gly Val Pro Gly Val
            100                 105                 110

Gly Val Pro Gly Phe Gly Val Pro Gly Val Gly Val Pro Gly Val Gly
        115                 120                 125

Val Pro Gly Val Gly Val Pro Gly Val Gly Val Pro Gly Phe Gly Val
    130                 135                 140

Pro Gly Val Gly Val Pro Gly Val Gly Val Pro Gly Val Gly Val Pro
145                 150                 155                 160

Gly Val Gly Val Pro Gly Phe Gly Val Pro Gly Val Gly Val Pro Gly
                165                 170                 175

Val Gly Val Pro Gly Val Gly Val Pro Gly Val Gly Val Pro Gly Phe
            180                 185                 190

Gly Val Pro Gly Val Gly Val Pro Gly Val Gly Val Pro Gly Val Gly
        195                 200                 205

Val Pro Gly Val Gly Val Pro Gly Phe Gly Val Pro Gly Val Gly Val
    210                 215                 220

Pro Gly Val Gly Val Pro Leu Glu Gly Ser Gly Thr Gly Ala Lys Leu
225                 230                 235                 240

<210> SEQ ID NO 17
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Arg Gly Ser His His His His His His Gly Ser Lys Pro Ile Ala
```

-continued

```
1               5                   10                  15
Ala Ser Ala Val Pro Gly Val Gly Val Pro Gly Val Gly Val Pro Gly
            20                  25                  30
Phe Gly Val Pro Gly Val Gly Val Pro Gly Val Gly Val Pro Gly Val
            35                  40                  45
Gly Val Pro Gly Val Gly Val Pro Gly Phe Gly Val Pro Gly Val Gly
            50                  55                  60
Val Pro Gly Val Gly Val Pro Gly Val Gly Val Pro Gly Val Gly Val
65                  70                  75                  80
Pro Gly Phe Gly Val Pro Gly Val Gly Val Pro Gly Val Gly Val Pro
            85                  90                  95
Gly Val Gly Val Pro Gly Val Gly Val Pro Gly Phe Gly Val Pro Gly
            100                 105                 110
Val Gly Val Pro Gly Val Gly Val Pro Gly Val Gly Val Pro Gly Val
            115                 120                 125
Gly Val Pro Gly Phe Gly Val Pro Gly Val Gly Val Pro Gly Val Gly
            130                 135                 140
Val Pro Leu Glu Gly Ser Glu Leu Ala Ala Thr Ala Thr Ala Thr Ala
145                 150                 155                 160
Thr Ala Thr Ala Thr Ala Ala Cys Gly Asp Leu Ala Pro Gln Met Leu
            165                 170                 175
Arg Glu Leu Gln Glu Thr Asn Ala Ala Leu Gln Asp Val Arg Glu Leu
            180                 185                 190
Leu Arg Gln Gln Val Lys Glu Ile Thr Phe Leu Lys Asn Thr Val Met
            195                 200                 205
Glu Ser Asp Ala Ser Gly Leu Gln Ala Ala Thr Ala Thr Ala Thr Ala
            210                 215                 220
Thr Ala Thr Ala Thr Ala Val Asp Lys Pro Ile Ala Ala Ser Ala Val
225                 230                 235                 240
Pro Gly Val Gly Val Pro Gly Val Gly Val Pro Gly Phe Gly Val Pro
            245                 250                 255
Gly Val Gly Val Pro Gly Val Gly Val Pro Gly Val Gly Val Pro Gly
            260                 265                 270
Val Gly Val Pro Gly Phe Gly Val Pro Gly Val Gly Val Pro Gly Val
            275                 280                 285
Gly Val Pro Gly Val Gly Val Pro Gly Val Gly Val Pro Gly Phe Gly
            290                 295                 300
Val Pro Gly Val Gly Val Pro Gly Val Gly Val Pro Gly Val Gly Val
305                 310                 315                 320
Pro Gly Val Gly Val Pro Gly Phe Gly Val Pro Gly Val Gly Val Pro
            325                 330                 335
Gly Val Gly Val Pro Gly Val Gly Val Pro Gly Val Gly Val Pro Gly
            340                 345                 350
Phe Gly Val Pro Gly Val Gly Val Pro Gly Val Gly Val Pro Leu Glu
            355                 360                 365
Gly Ser Gly Thr Gly Ala Lys Leu Asn
370                 375
```

POLYMER CARRIER

STATEMENT OF RELATED APPLICATION

This patent application is a division of U.S. patent application Ser. No. 13/163,299 having a filing date of 17 Jun. 2011, now U.S. Pat. No. 8,790,709, which is a continuation of U.S. patent application Ser. No. 12/141,192 having a filing date of 18 Jun. 2008, which claims priority on and the benefit of U.S. Provisional Patent Application No. 60/944,545 having a filing date of 18 Jun. 2007.

BACKGROUND OF THE INVENTION

1. Technical Field

This invention relates to carriers for bioactive agents. More particularly, this invention relates to a composition and method for delivering bioactive agents, such as vitamins, hormones, nutrients and drugs, by stabilizing and or solubilizing these agents in a polymer matrix. The polymers of this invention can be used for delivery of small molecules. The invention also relates to coatings or scaffolds for regenerative medicine.

2. Prior Art

Recombinant proteins are an emerging class of biopolymers. Such recombinant therapeutics have engendered advances in protein formulation and chemical modification, which can protect therapeutic molecules by blocking their exposure to proteolytic, oxidizing, or reducing enzymes. Protein modifications may also increase the therapeutic molecule's stability, circulation time, and biological activity. In the pharmaceutical industry, cosmetic industry, and other related industries, biopolymers are being used to deliver bioagents in controlled manners. The controlled release of bioactive agents can reduce the required frequency of administration or application by maintaining the concentration of the bioagent at desired levels. However, the delivery of bioactive agents has been hindered by the poor solubility or reactivity of the compounds.

Accordingly, there is always a need for an improved biopolymer or means for delivering bioactive agents. There also is a need for a carrier that can provide a means for protecting a small molecule to facilitate its solubilization in aqueous or physiologically buffered solutions. There further is a need for biomaterials that are biocompatible with the human body or other mammals and organisms and that may be used to promote tissue differentiation, for example, the release of vitamin D or other signaling factors. It is to these needs, among others, that this invention is directed.

BRIEF SUMMARY OF THE INVENTION

Briefly, this invention relates to a biologically derived polymer that can solubilize and protect small molecules from degradation. In one embodiment, a non-collagenous glycoprotein, for example cartilage oligomeric matrix protein (COMP), can be used as a protein carrier for various bioactive agents. An illustrative embodiment can utilize the regions composed of hydrophobic residues and form a hydrophobic pore with a threshold radius of 73 Å and a diameter that is 2-6 nm, this pore having the ability to store small hydrophobic molecules such for example as 1,25-dihydroxyvitamin $D_3$, cyclohexane, vitamin A, estradiol, and elaidic acid. A coiled-coil domain which is termed COMPcc is formed by component helices coming together to bury hydrophobic seams and the small molecule. As such, the carrier can be used to distribute small molecules without the need for another protein or linked moieties.

Embodiments of the present invention provide protein based encapsulators of small molecules. Other embodiments of the present invention bind to hydrophobic small molecules so as to encapsulate the hydrophobic small molecules and enable the small molecules to be delivered to certain locations. Another embodiment of the present invention utilizes COMPcc as the protein binding element.

It is contemplated that embodiments of this invention can have an array of applications. In the field of nutrition, the COMPcc carrier may provide a matrix for stabilization in vitamins and nutritional supplements, allowing for extended shelf life and efficacy. In the field of pharmaceuticals, the COMPcc carrier can help with solubilizing as well as stabilizing drugs and providing a delivery vehicle, and through mutation of the COMPcc sequence to tune the delivery kinetics of drugs. In regenerative medicine, the COMPcc carrier may fuse with other biopolymers to produce scaffold for tissue engineering.

The above features and many other features and advantages of this invention will become apparent from the following description of selected preferred embodiments, when read in conjunction with the accompanying drawings.

DETAILED DESCRIPTION OF PREFERRED EMBODIMENTS

Embodiments of this invention include a protein carrier or matrix and methods for delivering bioactive agents. More specifically, embodiments of the present invention provide protein based encapsulators of small molecules. Other embodiments of the present invention are protein based encapsulators that bind to hydrophobic small molecules so as to encapsulate the hydrophobic small molecules and enable the small molecules to be delivered to certain locations. A preferred illustrative embodiment of the present invention utilizes COMPcc as the protein binding element. Illustrative embodiments of this invention provide polymers that can be useful in preparing, for example, drug delivery devices and pharmaceutical compositions.

One illustrative embodiment can use a non-collagenous glycoprotein, for example cartilage oligomeric matrix protein (COMP), as a protein carrier for various bioactive agents. COMP is a 524 kDa homopentamer of five subunits that consists of an N-terminal heptad repeat region (cc) followed by four epidermal growth factor (EGF)-like domains, seven calcium-binding domains (T3), and a C-terminal globular domain (TC). COMP may be envisioned as a bouquet-like structure stabilized by interchain disulfide bonds in the N-terminal coiled-coil domain that contains residues 20-83. The N-terminal domain (COMPcc) is known for having a left-handed α-helical bundle with two C-terminal cysteine residues per monomer, which form the interchain di-sulfide bonds. This embodiment can make use of the structure of COMPcc or variants by itself or as fusions to other proteins, polymers, or fatty acids for improved efficacy.

Figure 1:
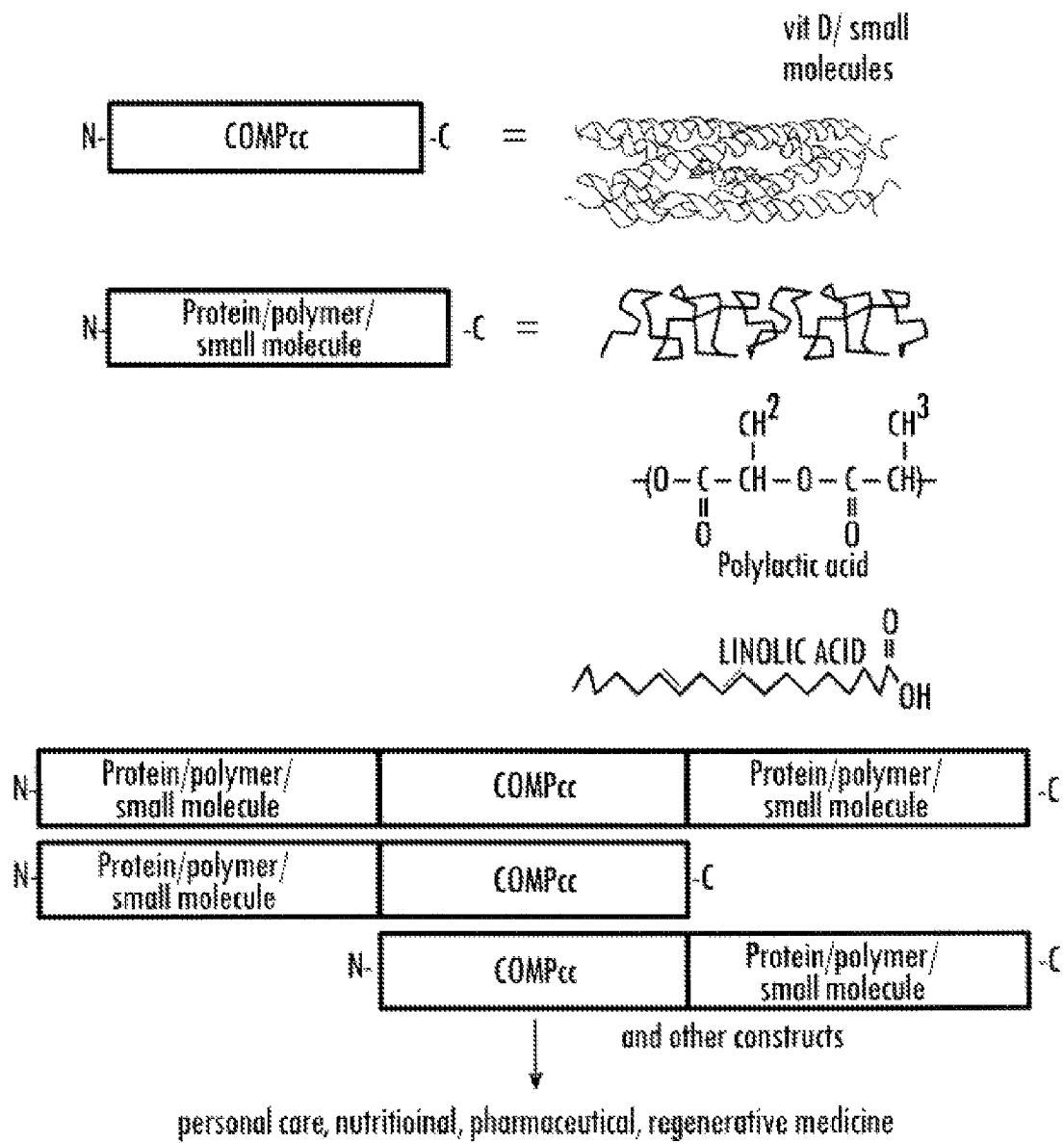
FIG. 1 is a figure showing the basic scheme of one embodiment of this invention.

As shown in FIG. 1, the protein carrier, according to one embodiment of this invention, can be used to safely solubilize small molecules. This illustrative embodiment can utilize the COMPcc region that is composed of hydrophobic residues and form a hydrophobic pore with a threshold radius of 73 Å and a diameter that is 2-6 nm. This pore can have the ability to store small hydrophobic molecules such as 1,25-dihydroxyvitamin $D_3$, cyclohexane, vitamin A (ATR), estradiol, and elaidic acid. The coiled-coil is a ubiquitous protein motif and the coiled-coil domain is formed by component helices coming together to bury hydrophobic seams and the small molecule. More specifically, as the hydrophobic seams twist around each helix, the helices also twist to coil around each other, thus burying the hydrophobic seams. As such, the carrier can be used to distribute small molecules without the need for another protein or linked moieties.

Further, it is possible to create a copolymer (or multipolymer) of the carrier (COMPcc or variant) by fusing the protein carrier to various proteins or ligands. For example, it is possible to fuse the carrier protein such as elastin, collagen, silk or keratin based sequences. In terms of application towards regenerative medicine, the COMPcc or variant likely can be linked to other proteins or synthetic polymers that provide the appropriate mechanical or biological properties. In such an embodiment, it is possible to incorporate components that will allow the production of tailor-made biopolymers suitable for tissue regeneration or surgical repair of various tissues.

Alternatively, it is possible to create covalent conjugation to other biocompatible and biodegradable polymers or small molecules such as PEG, PLA, PLGA or fatty acids. Accordingly, the carrier can be fused to the targeting moiety for optimal delivery or utility.

In another aspect of this embodiment, the carrier provides a nucleic acid sequence that is capable of encoding a fusion protein. The recombinant gene may be expressed and the polypeptide purified utilizing any number of methods. In one embodiment of this invention, the nucleic acid encoding the carrier can be fused with a receptor binding domain of a ligand.

A fusion polypeptide, according to preferred embodiments, includes functionally equivalent molecules in which amino acid residues are substituted for residues within the sequence resulting in a silent or conservative change. For example, one or more amino acid residues within the sequence can be substituted by another amino acid of a similar polarity that acts as a functional equivalent, resulting in a silent or conservative alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, for example, by glycosylation, proteolytic cleavage, and linkage to other ligands.

In terms of expression, the nucleic acid sequences encoding the carrier protein may be inserted into a recombinant vector, which may be plasmids, viruses or any other vehicle known in the art, that has been manipulated by the insertion or incorporation of the nucleic acid sequences encoding the chimeric peptides of the invention. The recombinant vector typically contains an origin of replication, a promoter, as well as specific genes that allow phenotypic selection of the transformed cells. Vectors suitable for use in the present invention include but are not limited to the T7-based expression vector for expression in bacteria or viral vectors for expression in mammalian cells, baculovirus-derived vectors for expression in insect cells, and cauliflower mosaic virus (CaMV), tobacco mosaic virus (TMV), and other vectors.

Depending on the vector utilized, any of a number of suitable transcription and translation elements, including constitutive and inducible promoters, transcription enhancer elements, transcription terminators, etcetera, may be used in the expression vector. Such construction of expression vectors and the expression of genes in transfected cells can involve the use of molecular cloning techniques (for example, in vitro recombinant DNA techniques, synthetic techniques, and in vivo recombination/genetic recombination), bacterial systems for the expression of vectors, yeast systems with constitutive or inducible promoters, insect systems, prokaryotic and eukaryotic systems using transfection or co-tranfections of DNA vectors, transgenic animals using for example viral infection, and embryonic stem cells. Methods and procedures for using and applying such vectors are widespread in publications and are known or easily obtainable by persons of ordinary skill in the art.

The carrier (along with the small molecule) of the present invention may be formulated with conventional pharmaceutical or veterinary mechanisms and materials. The carrier may be in conventional pharmaceutical administration forms such as powders, solutions, suspensions, dispersions, etcetera; however, solutions, suspensions, and dispersions in physiologically acceptable carrier media, for example water for injections, will generally be preferred. For example, such materials include emulsifiers, fatty acid esters, gelling agents, stabilizers, antioxidants, osmolality adjusting agents, buffers, preservatives, antimicrobial agents, and pH adjusting agents. Further, delivery mechanisms include parenteral administration (injection or infusion directly). The compositions according to the invention may therefore be formulated for administration using physiologically acceptable carriers or excipients in a manner fully within the skill level of the art.

The fusion polypeptides contemplated by the present invention may be purified by any technique that allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, any number of purification methods may be used, including but not limited to conventional ion exchange chromatography, affinity chromatography, different sugar chromatography, hydrophobic interaction chromatography, reverse phase chromatography, or gel filtration.

As disclosed previously, the proteins or variants of COMPcc may be used alone or as fusions to other proteins including elastin, collagen, silk, or keratin based sequences. In addition, covalent conjugation to other biocompatible and biodegradable polymers or small molecules such as PEG, PLA, PLGA, or fatty acids can be achieved. Such fusions can provide stability or improved characteristics for the particular objective (personal care, regenerative medicine, drug delivery, etcetera).

It is contemplated that embodiments of this invention can have an array of applications. In the field of nutrition, the COMPcc carrier may provide a matrix for stabilization in vitamins and nutritional supplements, allowing for extended shelf life and efficacy. In the field of pharmaceuticals, the COMPcc carrier can help with solubilizing as well as stabilizing drugs and providing a delivery vehicle, and through mutation of the COMPcc sequence to tune the delivery kinetics of drugs. In regenerative medicine, the COMPcc carrier may be fused with other biopolymers to produce scaffold for tissue engineering.

Generally, a cloned sequence of COMPcc useful for the present invention has an N-terminal histidine tag for facile purification into a Pqe9 vector was as follows:

```
                                          (SEQ ID NO: 1)
MRGSHHHHHHGSGDLAPQMLRELQETNAALQDVRELLRQQVKEITFLKNT

VMECDACGKLN
```

It also is possible to express in a different vector that does not necessarily bear the N-terminal histidine tag. The coiled-coil region of COMP has the following sequence:

```
                                          (SEQ ID NO: 2)
GDLAPQMLRELQETNAALQDVRELLRQQVKEITFLKNTVMECDACGKLN.
```

In these examples, the construct can be covalently attached to fatty acids, other polymers and/or can be fused with other proteins like elastin, silk, collagen, or keratin.

Preferably, the COMPcc homopolymer (and variants thereof) as well as block polymers of COMPcc are purified using conventional methods. Illustrative COMPcc sequences and their molecular weights that are suitable for use in the present invention are provided below.

COMPcc Homopolymer and Variants:

```
wt:
                                          (SEQ ID NO: 3)
MRGSHHHHHHGDLAPQMLRELQETNAALQDVRELLRQQVKEITFLKNTV

MECDACGKLN [6.9 KDa]

S:
                                          (SEQ ID NO: 4)
MRGSHHHHHHGDLAPQMLRELQETNAALQDVRELLRQQVKEITFLKNTV

MESDASGKLN [6.9 KDa]

L37A:
                                          (SEQ ID NO: 5)
MRGSHHHHHHGDLAPQMLREAQETNAALQDVRELLRQQVKEITFLKN

TVMESDASGKLN [6.9 KDa]

T40A:
                                          (SEQ ID NO: 6)
MRGSHHHHHHGDLAPQMLRELQEANAALQDVRELLRQQVKEITFLKN

TVMESDASGKLN [6.9 KDa]

L44A:
                                          (SEQ ID NO: 7)
MRGSHHHHHHGDLAPQMLRELQETNAAAQDVRELLRQQVKEITFLKN

TVMESDASGKLN [6.9 KDa]

L47A:
                                          (SEQ ID NO: 8)
MRGSHHHHHHGDLAPQMLRELQETNAALQDARELLRQQVKEITFLKN

TVMESDASGKLN [6.9 KDa]

L51A:
                                          (SEQ ID NO: 9)
MRGSHHHHHHGDLAPQMLRELQETNAALQDVRELARQQVKEITFLKN

TVMESDASGKLN [6.9 KDa]

Q54A:
                                          (SEQ ID NO: 10)
MRGSHHHHHHGDLAPQMLRELQETNAALQDVRELLRQAVKEITFLKN

TVMESDASGKLN [6.9 KDa]

I58A:
                                          (SEQ ID NO: 11)
MRGSHHHHHHGDLAPQMLRELQETNAALQDVRELLRQQVKEATFLKN

TVMESDASGKLN [6.9 KDa]

L61A:
                                          (SEQ ID NO: 12)
MRGSHHHHHHGDLAPQMLRELQETNAALQDVRELLRQQVKEITFAKN

TVMESDASGKLN [6.9 KDa]

V65A:
                                          (SEQ ID NO 13)
MRGSHHHHHHGDLAPQMLRELQETNAALQDVRELLRQQVKEITFLKN

TAMESDASGKLN [6.9 KDa]

S65A:
                                          (SEQ ID NO: 14)
MRGSHHHHHHGDLAPQMLRELQETNAALQDVRELLRQQVKEITFLKN

TVMEADASGKLN [6.9 KDa]
```

COMPcc Block Polymers:

```
                                                     (SEQ ID NO: 15)
Elastin-COMPcc--MRGSHHHHHG S K P I A A S A V P G V G V P G V G V

P G F G V P G V G V P G V G V P G V G V P G V G V P G F G V P G V G V

P G V G V P G V G V P G V G V P G F G V P G V G V P G V G V P G V G V

P G V G V P G F G V P G V G V P G V G V P G V G V P G V G V P G F G V
```

-continued

```
P G V G V P G V G V P L E G S E L A A T A T A T A T A T A A C G D L A

P Q Met L R E L Q E T N A A L Q D V R E L L R Q Q V K E I T F L K N T V

Met E S D A S G L Q A A T A T A T A T A T A V D L Q P S
[22.38 KDa]
```

(SEQ ID NO: 16)
```
COMPcc-Elastin--MRGSHHHHHHG S A C E L A A T A T A T A T A T A A C G D L A P Q Met L R E L Q E T N A A L Q D V R E L L R Q Q V K E I T F L K N T V Met E S D A S G L Q A A T A T A T A T A T A V D K P I A A S A

V P G V G V P G V G V P G F G V P G V G V P G V G V P G V G V P G V G

V P G F G V P G V G V P G V G V P G V G V P G V G V P G F G V P G V G

V P G V G V P G V G V P G V G V P G F G V P G V G V P G V G V P G V G

V P G V G V P G F G V P G V G V P G V G V P L E G S G T G A K L
[22.65 KDa]
```

(SEQ ID NO: 17)
```
Eastin-COMPcc-Elastin--MRGSHHHHHHG S K P I A A S A V P G V G V P G

V G V P G F G V P G V G V P G V G V P G V G V P G V G V P G F G V P G

V G V P G V G V P G V G V P G V G V P G F G V P G V G V P G V G V P G

V G V P G V G V P G F G V P G V G V P G V G V P G V G V P G V G V P G

F G V P G V G V P G V G V P L E G S E L A A T A T A T A T A T A A C

G D L A P Q Met L R E L Q E T N A A L Q D V R E L L R Q Q V K E I T F L K

N T V Met E S D A S G L Q A A T A T A T A T A T A V D K P I A A S A V

P G V G V P G V G V P G F G V P G V G V P G V G V P G V G V P G V G V

P G F G V P G V G V P G V G V P G V G V P G V G V P G F G V P G V G V

P G V G V P G V G V P G V G V P G F G V P G V G V P G V G V P G V G V

P G V G V P G F G V P G V G V P G V G V P L E G S G T G A K L N
[34.17 KDa]
```

Figure 3:
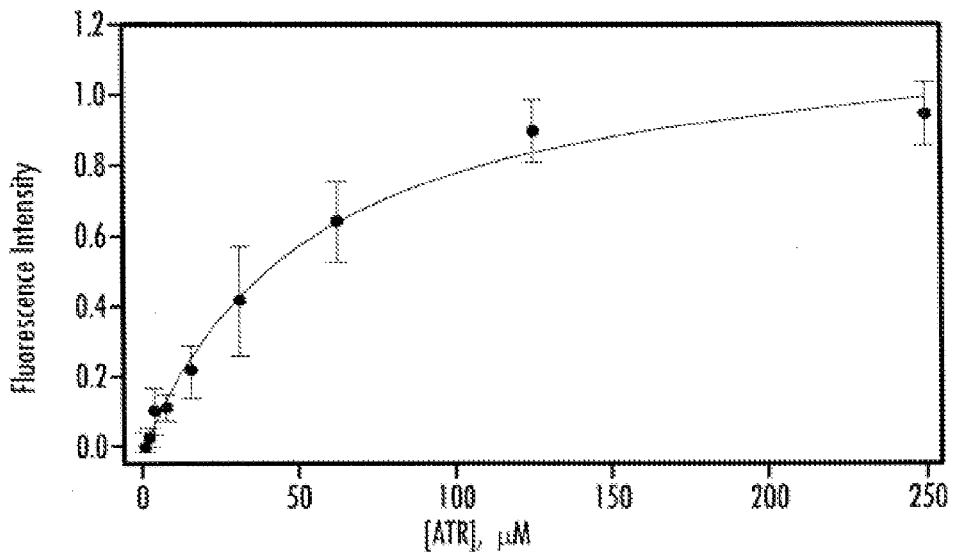
FIG. 3 illustrates fluorescence intensity as a function of ATR concentration for COMPcc.
Figure 4:
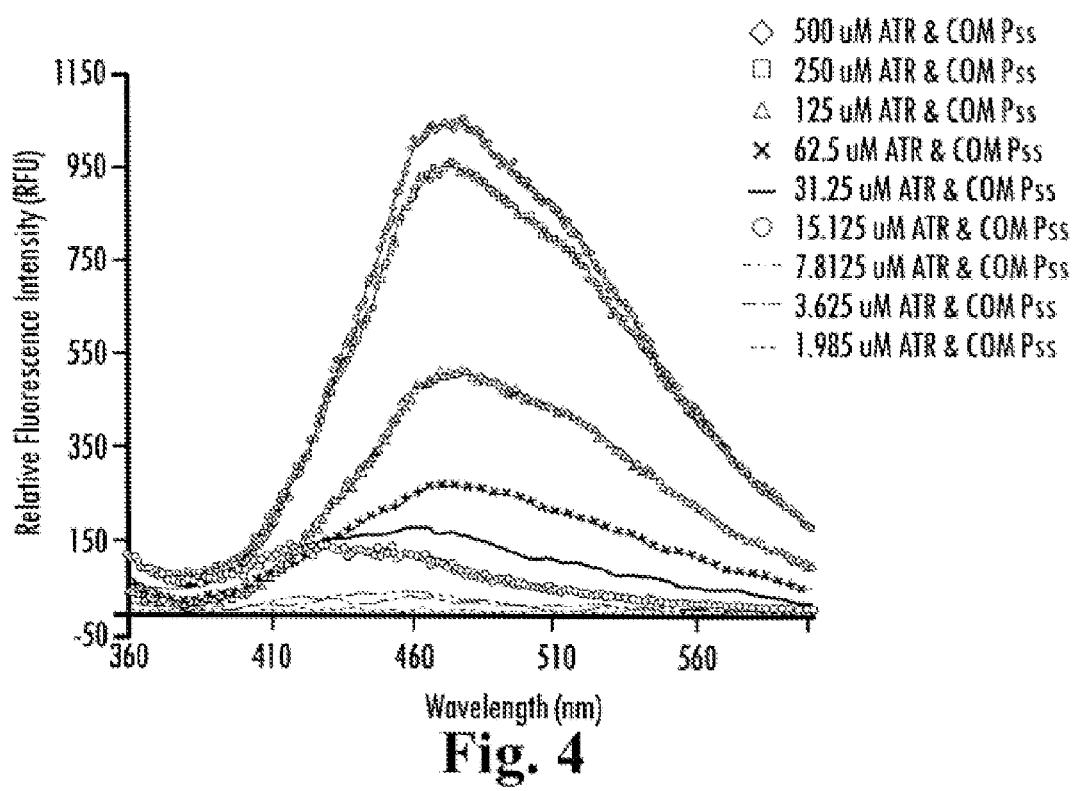
FIG. 4 illustrates fluorescence experiments investigating ATR binding to the S variant of COMPcc, showing the relative fluorescence intensity versus the wavelength.
Figure 5:
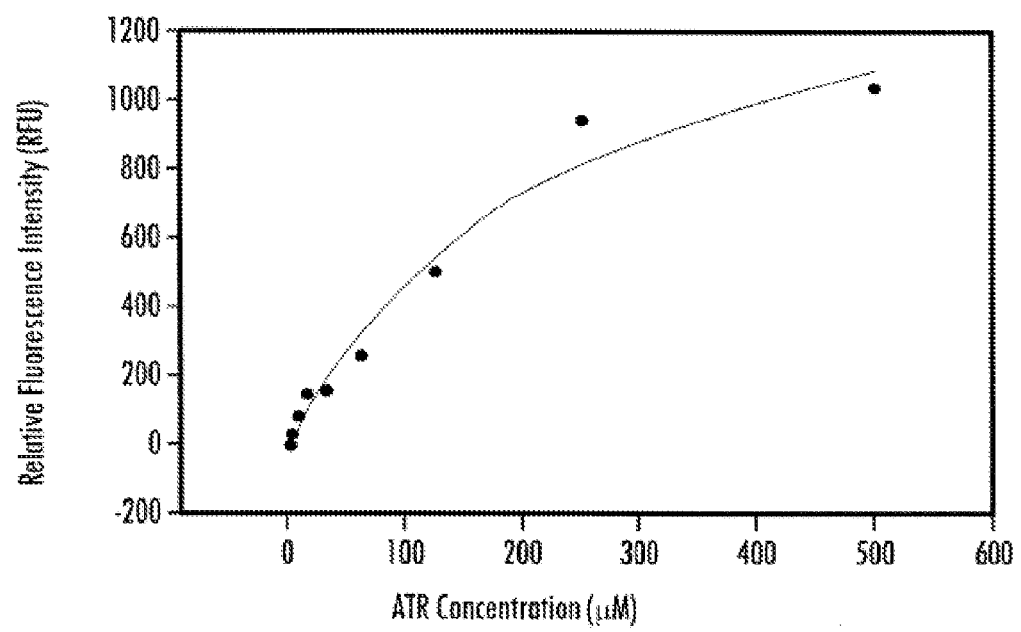
FIG. 5 illustrates fluorescence intensity as a function of ATR concentration for COMPcc.
Figure 6:
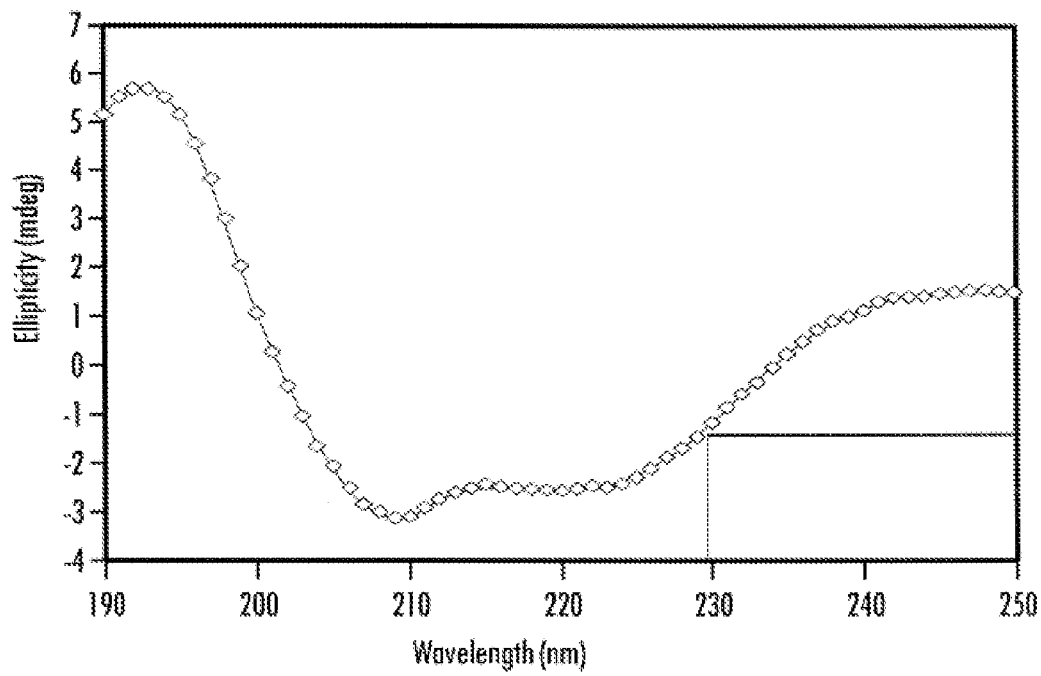
FIG. 6 illustrates circular dichroism data for COMPcc.
Figure 7:
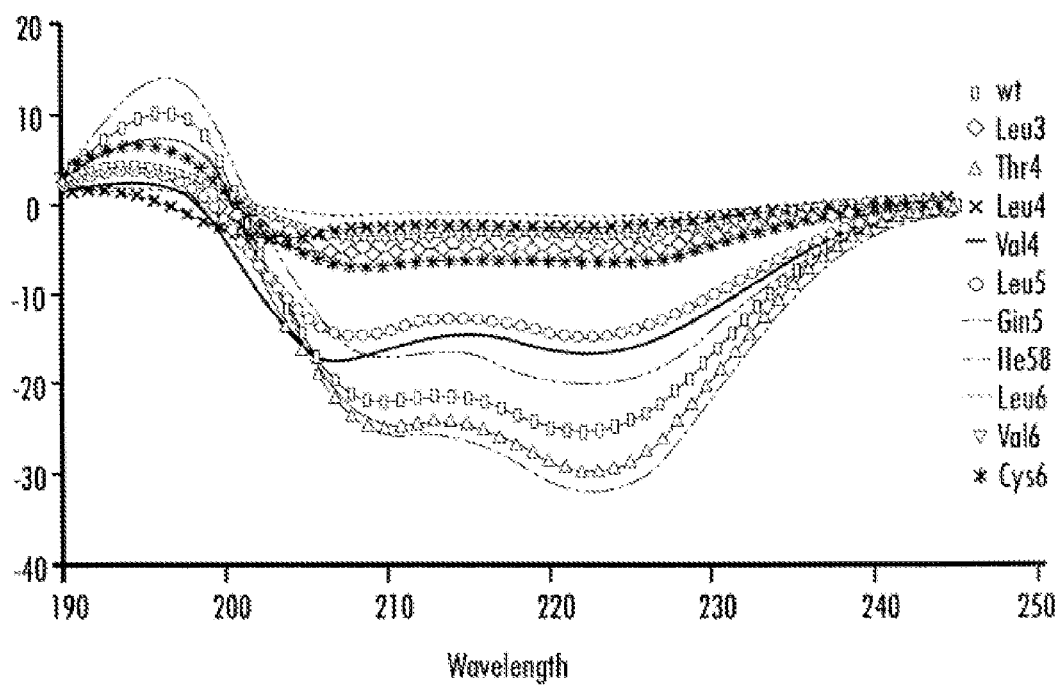
FIG. 7 illustrates circular dichroism data for COMPcc variants.

Fluorescence binding studies were conducted for binding ATR to COMP to illustrate and identify the small molecule binding by wild-type (FIGS. 2 and 3) and the S variant of COMPcc (FIGS. 4 and 5). The fluorescence experiments with ATR indicates binding of the bioactive agent, in these illustrative examples, ATR (all transretinol), which is also known to be Vitamin A. It can also bind Vitamin D and potentially other biomolecules, such as but not limited to hormones, nutrients and drugs, which other biomolecules can be determined by those of ordinary skill in the art without undue experimentation based, in part, on the invention's ability to bind Vitamins A and D.

Figure 2:
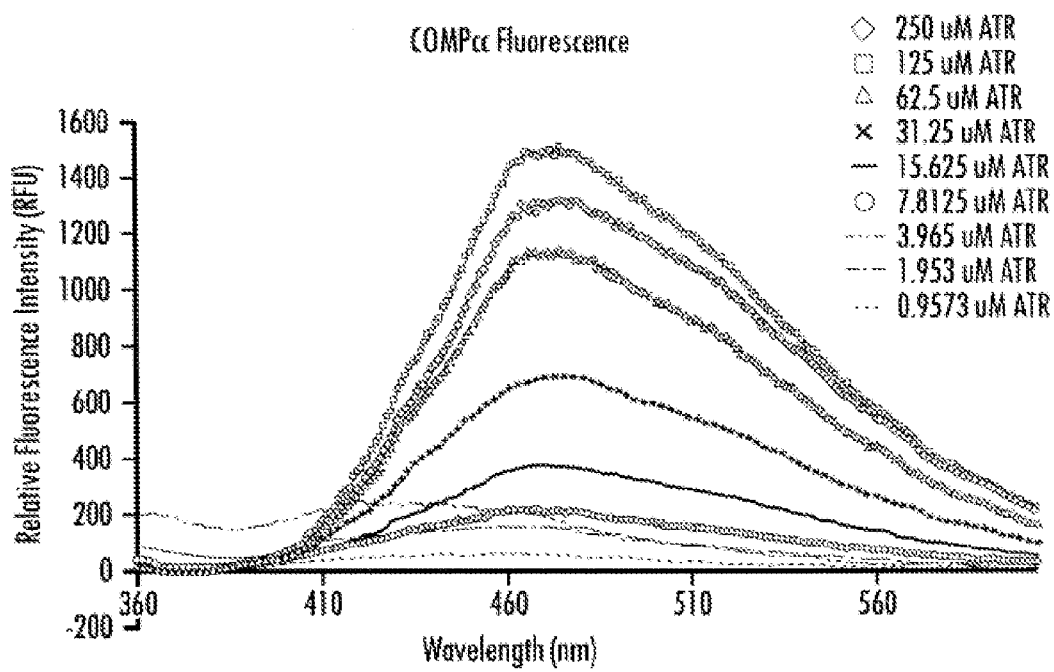
FIG. 2 illustrates fluorescence experiments investigating ATR binding to COMPcc, showing the relative fluorescence intensity versus the wavelength.
Figure 8:
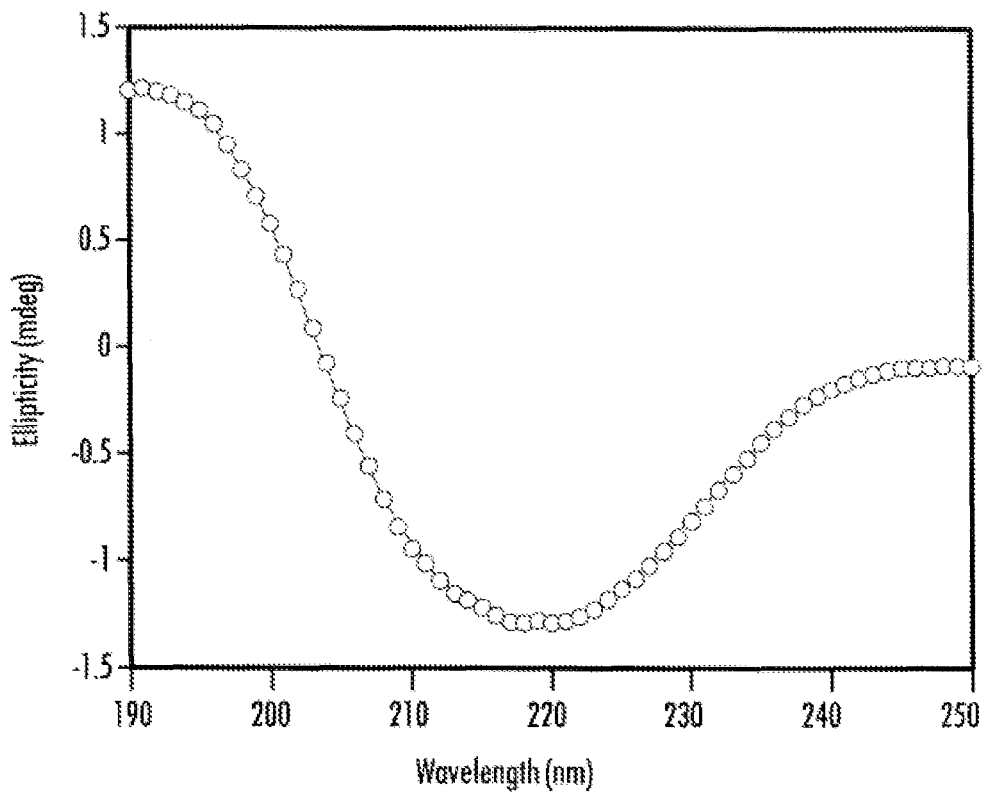
FIG. 8 illustrates circular dichroism data for Elastin.

FIGS. 2 and 3 illustrate fluorescence experiments investigating ATR binding to COMPcc. Approximately 9 μM COMPcc was used to bind a range of ATR concentrations. These experiments were done in PBS buffer under pH 7.6, and the reading was taken after two minutes and monitored over time. The high RFU values indicate encapsulation of ATR to the hydrophobic pore of COMPcc. FIG. 2 illustrates the relative fluorescence intensity versus the wavelength and FIG. 3 illustrates the fluorescence intensity versus the ATR concentration. FIG. 3 also illustrates the determination of binding dissociation constants for ATR binding to COMPcc. The binding curve shown is from three different trials performed on different days. The data shows a dissociation constant of 39.98 μM ATR, with a molar ratio of 4.44 of ATR to protein. Thus, at 39.98 μM ATR for 9 μM protein, 50% of the small molecule ATR binds to hydrophobic pore of the protein.

FIGS. 4 and 5 illustrate fluorescence experiments investigating ATR binding to the S variant of COMPcc under conditions similar to those disclose above in connection with FIGS. 2 and 3 for COMPcc. FIG. 4 illustrates the relative fluorescence intensity versus the wavelength and FIG. 5 illustrates the fluorescence intensity versus the ATR concentration.

TABLE 1

| Kd after 2 min | Kd after 4 hrs | Kd after 7 hrs | Kd after 10 hrs | Kd after 29 hrs |
|---|---|---|---|---|
| 34.6 μM $R^2 = 0.969$ | 39.7 μM $R^2 = 0.958$ | 42.7 μM $R^2 = 0.9543$ | 50.0 μM $R^2 = 0.9073$ | 61.55 μM $R^2 = 0.870$ |

Table 1 illustrates COMPcc incubated with retinol at various time periods to achieve optimal encapsulation over time. The dissociation constants for 50% binding of ATR to COMPcc are shown, and how it is maintained over a period of 29 hours. The $R^2$ values indicate a good the fit for the Kd values over time.

Structural Analysis of COMP and COMP Variants.

FIG. 6 illustrates the circular dichroism data for COMPcc with serine residues showing double minima at 208 nm and 222 nm. FIG. 7 illustrates the circular dichroism data for COMPcc variants showing double minima at 208 nm and 222 nm. Depending on the mutation, an improved or loss in structure is observed. FIG. 8 illustrates the circular dichroism data for Elastin with a single minima between 210 nm and 222 nm. These data show that the expected alpha-helical structure is achieved.

Structure of Block Co-Polymers of ELP-COMPcc

Figure 9:
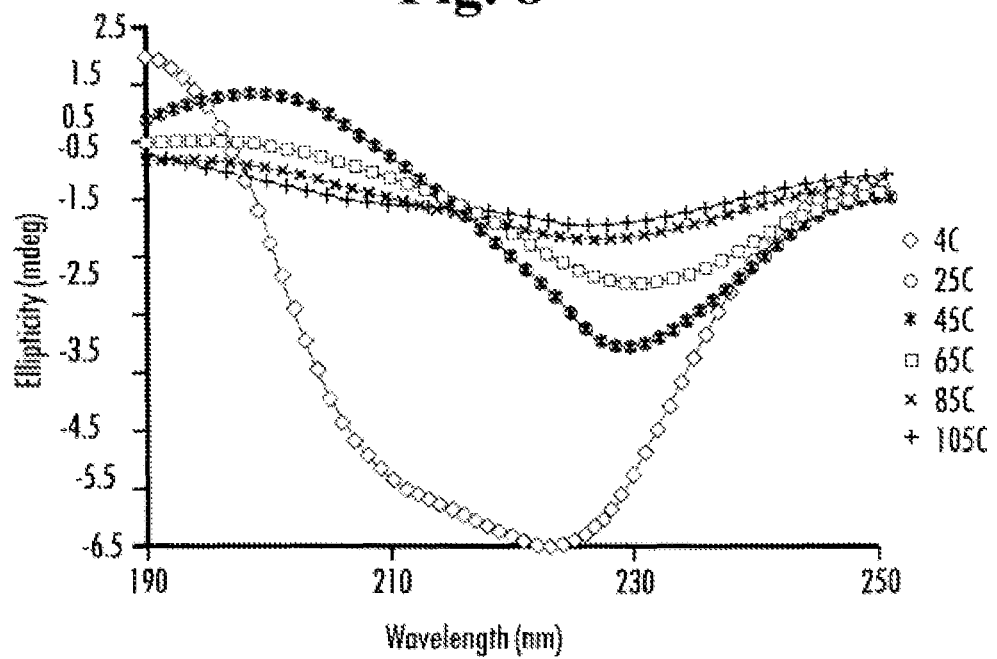
FIG. 9 illustrates circular dichroism data for Elastin-COMPcc at a series of temperatures ranging from 4° C. to 105° C.

FIG. 9 illustrates the circular dichroism data for Elastin-COMPcc at a series of temperatures ranging from 4° C. to 105° C. At lower temperatures there is evidence for the behavior of the alpha-helix because there is a double minima. At higher temperatures there is evidence for the behavior of beta spiral because there is a single minima. These data show a temperature dependent conformational change that may be tunable for future delivery of the bioactive cargo.

Figure 10:
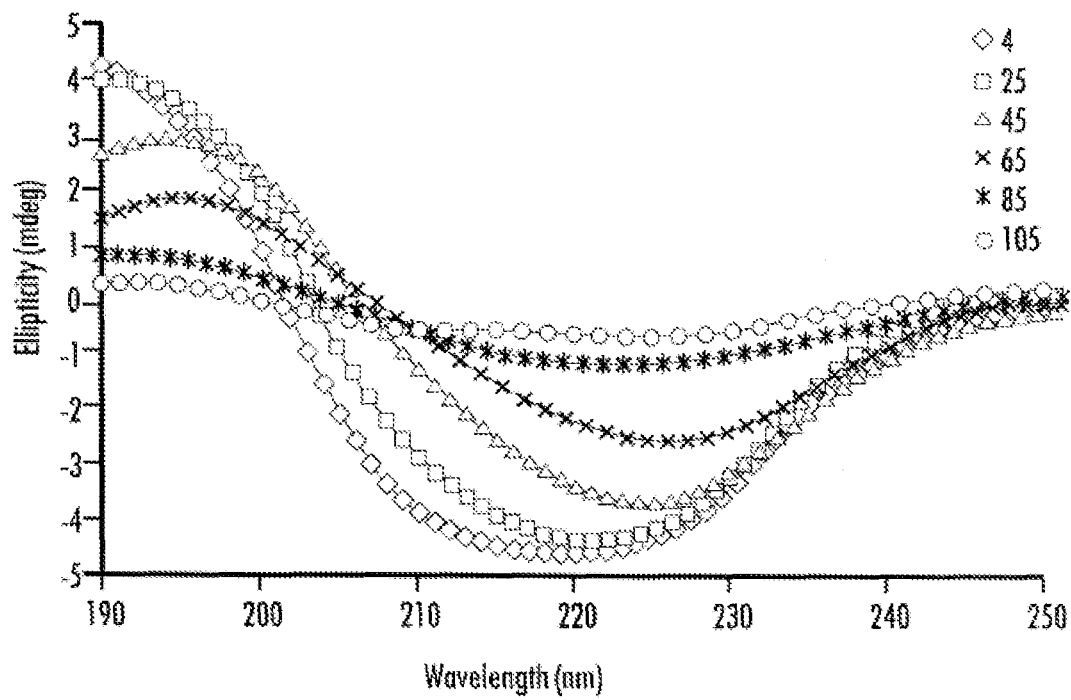
FIG. 10 illustrates circular dichroism data for COMPcc-Elastin at a series of temperatures ranging from 4° C. to 105° C.

FIG. 10 illustrates the circular dichroism data for COM-Pcc-Elastin at a series of temperatures ranging from 4° C. to 105° C. At lower temperatures there is evidence for the behavior of the alpha-helix because there is a double minima. At higher temperatures there is evidence for the behavior of beta spiral because there is a single minima. These data show a temperature dependent conformational change that may be tunable for future delivery of the bioactive cargo.

Figure 11:
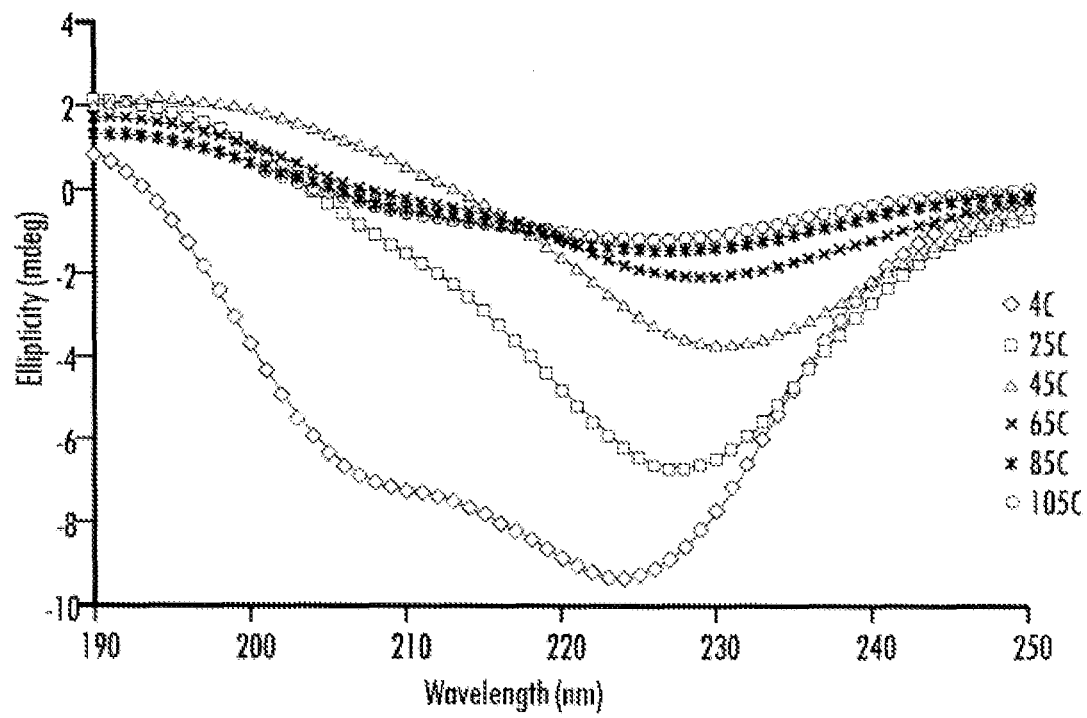
FIG. 11 illustrates circular dichroism data for Elastin-COMPcc-Elastin with at a series of temperatures ranging from 4° C. to 105° C.

FIG. 11 illustrates the circular dichroism data for Elastin-COMPcc-Elastin at a series of temperatures ranging from 4° C. to 105° C. At lower temperatures there is evidence for the behavior of the alpha-helix because there is a double minima. At higher temperatures there is evidence for the behavior of beta spiral because there is a single minima. These data show a temperature dependent conformational change that may be tunable for future delivery of the bioactive cargo.

Tri-Block AFM Evidence for Elasticity

Figure 12:
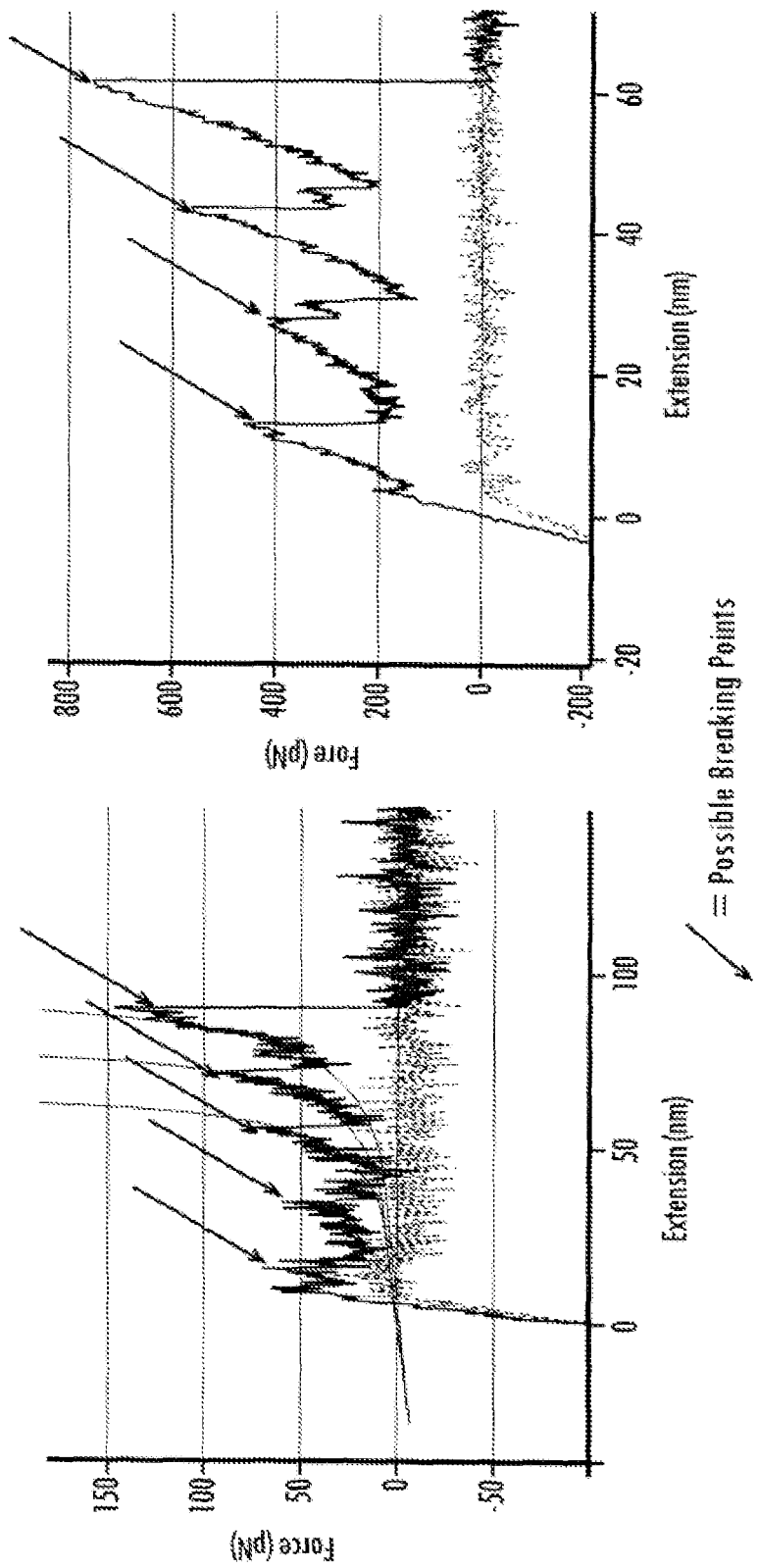
FIG. 12 illustrates AFM data for Elastin-COMPcc-Elastin.

FIG. 12 illustrates the AFM data for Elastin-COMPcc-Elastin indicating elasticity of repeats in the tri-block sequence because of the possible breaking points present. These data show that these materials are structured and may be used as suitable scaffolds for regenerative medicine.

The above description sets forth the best mode of the invention as known to the inventor at this time, and is for illustrative purposes only, as it is obvious to one skilled in the art to make modifications to this process without departing from the spirit and scope of the invention and its equivalents as set forth in the appended claims.

What is claimed is:

1. A method for encapsulating a hydrophobic small molecule comprising:
   combining a carrier polymer, wherein the carrier polymer comprises an amino acid sequence selected from the group consisting of SEQ ID NOS: 3-17 and forms a hydrophobic pore with a threshold radius of 73 Å and a diameter that is 2-6 nm, and a hydrophobic small molecule, wherein the hydrophobic small molecule binds to and is encapsulated by the hydrophobic pore of the carrier polymer so as to form an encapsulated hydrophobic small molecule.

2. The method of claim 1, further comprising formulating the carrier polymer having one or more hydrophobic small molecules encapsulated therein with pharmaceutical or veterinary materials in a form selected from the group consisting of powders, solutions, suspensions, and dispersions.

3. The method of claim 1, further comprising utilizing the carrier polymer having one or more hydrophobic small molecules encapsulated therein as a carrier for delivery of the encapsulated hydrophobic small molecule.

4. The method of claim 1, further comprising formulating the carrier polymer having one or more hydrophobic small molecules encapsulated therein with emulsifiers, fatty acid esters, gelling agents, stabilizers, antioxidants, osmolality adjusting agents, buffers, preservatives, antimicrobial agents, and/or pH adjusting agents.

5. A method for encapsulating a hydrophobic small molecule comprising:
   combining:
   a) a carrier polymer, wherein the carrier polymer comprises an amino acid sequence which is a variant of SEQ ID NO: 2, wherein the variant is selected from the group consisting of:
      i.) SEQ ID NO: 2, wherein the cysteine at position 42 is replaced with a serine and the cysteine at position 45 is replaced with a serine,
      ii.) SEQ ID NO: 2, wherein the leucine at position 11 is replaced with an alanine, the cysteine at position 42 is replaced with a serine, and the cysteine at position 45 is replaced with a serine,
      iii.) SEQ ID NO: 2, wherein the threonine at position 14 is replaced with an alanine, the cysteine at position 42 is replaced with a serine, and the cysteine at position 45 is replaced with a serine,
      iv.) SEQ ID NO: 2, wherein the leucine at position 18 is replaced with an alanine, the cysteine at position 42 is replaced with a serine, and the cysteine at position 45 is replaced with a serine,
      v.) SEQ ID NO: 2, wherein the valine at position 21 is replaced with an alanine, the cysteine at position 42 is replaced with a serine, and the cysteine at position 45 is replaced with a serine,
      vi.) SEQ ID NO: 2, wherein the leucine at position 25 is replaced with an alanine, the cysteine at position 42 is replaced with a serine, and the cysteine at position 45 is replaced with a serine,
      vii.) SEQ ID NO: 2, wherein the glutamine at position 28 is replaced with an alanine, the cysteine at position 42 is replaced with a serine and the cysteine at position 45 is replaced with a serine,
      viii.) SEQ ID NO: 2, wherein the isoleucine at position 32 is replaced with an alanine, the cysteine at position 42 is replaced with a serine and the cysteine at position 45 is replaced with a serine,
      ix.) SEQ ID NO: 2, wherein the leucine at position 35 is replaced with an alanine, the cysteine at position 42 is replaced with a serine and the cysteine at position 45 is replaced with a serine,
      x.) SEQ ID NO: 2, wherein the valine at position 39 is replaced with an alanine, the cysteine at position 42 is replaced with a serine and the cysteine at position 45 is replaced with a serine, and
      xi.) SEQ ID NO: 2, wherein the cysteine at position 42 is replaced with an alanine and the cysteine at position 45 is replaced with a serine,
   and forms a hydrophobic pore with a threshold radius of 73 Å and a diameter that is 2-6 nm, and
   b) a hydrophobic small molecule,
   wherein the hydrophobic small molecule binds to and is encapsulated by the hydrophobic pore of the carrier polymer so as to form an encapsulated carrier polymer.

6. The method of claim 5, further comprising formulating the encapsulated hydrophobic small molecule with conventional pharmaceutical or veterinary materials in a form selected from the group consisting of powders, solutions, suspensions, and dispersions.

7. The method of claim 5, further comprising utilizing the carrier polymer having one or more hydrophobic small molecules as a carrier for delivery of the encapsulated hydrophobic small molecules.

8. The method of claim 5, further comprising formulating the carrier polymer having one or more hydrophobic small molecules encapsulated therein with emulsifiers, fatty acid esters, gelling agents, stabilizers, antioxidants, osmolality adjusting agents, buffers, preservatives, antimicrobial agents, and/or pH adjusting agents.

9. A method for encapsulating a hydrophobic small molecule comprising:
   combining a carrier polymer comprising a fusion protein comprising:
   a) amino acid sequence SEQ ID NO: 2, or a variant thereof, wherein the variant has an amino acid sequence selected from the group consisting of:
      i) SEQ ID NO: 2, wherein the cysteine at position 42 is replaced with a serine and the cysteine at position 45 is replaced with a serine,
      ii.) SEQ ID NO: 2, wherein the leucine at position 11 is replaced with an alanine, the cysteine at position 42 is replaced with a serine, and the cysteine at position 45 is replaced with a serine,
      iii.) SEQ ID NO: 2, wherein the threonine at position 14 is replaced with an alanine, the cysteine at position 42 is replaced with a serine, and the cysteine at position 45 is replaced with a serine,
      iv.) SEQ ID NO: 2, wherein the leucine at position 18 is replaced with an alanine, the cysteine at position 42 is replaced with a serine, and the cysteine at position 45 is replaced with a serine,
      v.) SEQ ID NO: 2, wherein the valine at position 21 is replaced with an alanine, the cysteine at position 42 is replaced with a serine, and the cysteine at position 45 is replaced with a serine,
      vi.) SEQ ID NO: 2, wherein the leucine at position 25 is replaced with an alanine, the cysteine at position 42 is replaced with a serine, and the cysteine at position 45 is replaced with a serine,
      vii.) SEQ ID NO: 2, wherein the glutamine at position 28 is replaced with an alanine, the cysteine at position 42 is replaced with a serine and the cysteine at position 45 is replaced with a serine, viii.) SEQ ID NO: 2, wherein the isoleucine at position 32 is replaced with an alanine, the cysteine at position 42 is replaced with a serine and the cysteine at position 45 is replaced with a serine, ix.) SEQ ID NO: 2, wherein the leucine at position 35 is replaced with an alanine, the cysteine at position 42 is replaced with a serine and the cysteine at position 45 is replaced with a serine, x.) SEQ ID NO: 2, wherein the valine at position 39 is replaced with an alanine, the cysteine at position 42 is replaced with a serine and the cysteine at position 45 is replaced with a serine, and xi.) SEQ ID NO: 2, wherein the cysteine at position 42 is replaced with an alanine and the cysteine at position 45 is replaced with a serine, and b) elastin, collagen, silk or keratin, wherein the amino acid sequence SEQ ID NO: 2, or the variant thereof, is covalently bonded to the elastin, collagen, silk or keratin, and the fusion protein forms a hydrophobic pore with a threshold radius of 73 Å and a diameter that is 2-6 nm, and a hydrophobic small molecule, wherein the hydrophobic small molecule binds to and is encapsulated by the hydrophobic pore of the carrier polymer so as to form an encapsulated hydrophobic small molecule.

10. The method of claim 9, wherein the fusion protein comprises an amino acid sequence selected from the group consisting of SEQ ID NOS: 7-15.

11. The method of claim 9, further comprising formulating the encapsulated hydrophobic small molecule with pharmaceutical or veterinary materials in a form selected from the group consisting of powders, solutions, suspensions, and dispersions.

12. The method of claim 9, further comprising utilizing the carrier polymer having one or more hydrophobic small molecules encapsulated therein as a carrier for delivery of the encapsulated hydrophobic small molecules.

13. The method of claim 9, further comprising formulating the carrier polymer having one or more hydrophobic small molecules encapsulated therein with emulsifiers, fatty acid esters, gelling agents, stabilizers, antioxidants, osmolality adjusting agents, buffers, preservatives, antimicrobial agents, and/or pH adjusting agents.

* * * * *